United States Patent [19]

Miyazono et al.

[11] Patent Number: 5,280,109
[45] Date of Patent: Jan. 18, 1994

[54] ISOLATED, LARGE LATENT COMPLEXES OF TGF-β2 AND TGF-β3, AND NEW BINDING PROTEIN FOR LATENT FORM TGF-β1, TGF-β2 AND TGF-β3 LTBP-2

[75] Inventors: Kohei Miyazono; Carl-Henrik Heldin; Anders Olofsson, all of Uppsala, Sweden

[73] Assignee: Ludwig Institute for Cancer Research, N.Y.

[21] Appl. No.: 826,577

[22] Filed: Jan. 27, 1992

[51] Int. Cl.$^5$ .............................................. C07K 13/00
[52] U.S. Cl. .................................. 530/399; 530/413; 530/389.1; 530/389.2
[58] Field of Search .................. 530/399, 413, 387

[56] References Cited

FOREIGN PATENT DOCUMENTS

WO9113152 9/1991 PCT Int'l Appl. .

OTHER PUBLICATIONS

Okada et al. *J. Biochem* 106:304–310 (1989).
Miyazono et al. *EMBO J.* 10(5): 1091–1101 (1991).
Gentry et al. *Mol. Cell. Biol* 7(10): 3418–3427 (1987).
Wakefield et al. *J. Cell Biol.* 105:965–975 (1987).
Pirches et al. *Cancer Res* 44:5538–5543 (1984).
Cheiftetz et al. *Cell* 48:409–415 (1987).
Madisen et al. *DNA* 7:1–8 (1988).
Kanzaki et al., Cell 61:1057–1061 (Jun. 15, 1990).
Miyazono et al., Nature 338: (621): 158–160 (Mar. 9, 1989).
Wakefield et al., J. Biol. Chem. 263(16): 7646–7654 (Jun. 5, 1988).
Miyazono et al., J. Biol. Chem. 263(13): 6407–6415 (May 5, 1988).

Primary Examiner—Robert J. Hill, Jr.
Assistant Examiner—Shelly Guest Cermak
Attorney, Agent, or Firm—Felfe & Lynch

[57] ABSTRACT

The invention relates to large latent complexes of TGF-β2 and TGF-β3, and methods for Isolating these. The complex consists of a dimerized form of TGF-β2 or TGF-β3, the appropriate latency associated peptide, and the latent TGF-β1 binding protein, referred to as LTBP. Also described is a protein which binds to all of TGF-β1, TGF-β2 and TGF-β3, but is immunologically distinct from LTBP, referred to as LTBP-2.

3 Claims, 8 Drawing Sheets

FIG. 2A

FIG. 2B fraction  8 10 12 14 16 18 20 22 24 26
anti LTBP

FIG. 2C fraction  8 10 12 14 16 18 20 22 24 26
anti ß1-LAP

FIG. 2D fraction  8 10 12 14 16 18 20 22 24 26
anti ß2-LAP

FIG. 2E fraction  8 10 12 14 16 18 20 22 24 26
anti ß3-LAP

ISOLATED, LARGE LATENT COMPLEXES OF TGF-β2 AND TGF-β3, AND NEW BINDING PROTEIN FOR LATENT FORM TGF-β1, TGF-β2 AND TGF-β3 LTBP-2

FIELD OF THE INVENTION

This invention refers to the family of molecules known as the transforming growth factor betas, or "TGF-βs". More specifically, it refers to new complexes of these molecules, sometimes referred to as "large latent" or "LL" complexes. The invention also relates to a newly recognized component of such "LL" complexes, referred to as "LTBP-2".

BACKGROUND OF THE INVENTION

Transforming growth factor beta, or "TGF-β" as used hereafter, refers to a family of multifunctional, dimeric polypeptides having a molecular weight of about 25000 daltons. See U.S. Pat. No. 4,931,548 to Lucas et al., the disclosure of which is incorporated by reference, as well as Lyons et al., Eur. J. Biochem 187: 467–473 (1990); Massagué, Ann. Rev. Cell Biol. 6: 597–641 (1990); Roberts et al., in Peptide Growth Factors And Their Receptors, part 1 (Sporn et al., ed), pp. 419–472 (1990); Sporn et al., Science 233: 532–534 (1986); Massagué, Trends in Biochem. Sci. 10: 239–240 (1985). The TGF-βs have been found to stimulate certain cell types and to inhibit others with respect to cell growth and differentiation. They also influence adipogenesis, myogenesis, chondrogenesis, osteogenesis, epithelial cell differentiation and immune cell function. See Lucas et al., supra.

At least three related isoforms of TGF-β have been identified, i.e., "TGF-β1, TGF-β2 and TGF-β3". Although related, their properties are not identical, as summarized by, e.g., Graycar et al., Mol. Endrocrinol 3: 1977–1986 (1989), Cheifetz et al., J. Biol. Chem. 265: 20533–10538 (1990). Promoter regions of the three isoforms vary considerably, and their production is differently regulated, as pointed out by Roberts et al., Ciba Found. Symp. 157: 7–28 (1991).

TGF-β molecules have been observed to be produced in an inactive, high molecular weight forms. For example, TGF-β1, isolated from human and rat platelets, have been found as a complex of three components, referred to hereafter as the "large latent complex", the "LL" complex or "LLTGF-β1". This complex consists of a dimer of the active TGF-β1 molecule, i.e., the 25 KDa structure referred to supra. It also includes a molecular moiety referred to as the "latency associated peptide" or "β1-LAP", and a larger molecule, referred to as the latent TGF-β1 binding protein or "LTBP". As to the high molecular weight forms, see Pircher et al., Canc. Res. 44: 5538–5543 (1984); Wakefield et al., J. Cell Biol. 105: 965–975 (1987). As to β1-LAP and LTBP, see Miyazono et al., J. Biol. Chem. 263: 6407–6415 (1988); Wakefield et al., J. Biol. Chem. 263: 7646–7654 (1988); and Okada et al., J. Biochem 106: 304–310 (1989). Latent TGF-β1 can be activated in vitro via various physical and chemical treatments or by exposure to low or high pH (Brown et al., Growth Factors 3: 35–43 (1990)). The activating mechanism in vivo remains unclear, but may involve enzymatic digestion, as suggested by Miyazono et al., Ciba Found. Symp. 57: 81–89 (1991).

The three recognized forms of TGF-β have been produced, in recombinant form, where each form of TGF-β dimer is non covalently associated with the β-LAP. These complexes are inactive, have a molecular mass of about 100 KDa, and are activated to produce the mature and active TGF-β dimer. See Brown, supra; Gentry et al., Mol. Cell Biol. 7: 3418–3427 (1987). The complex of TGF-β and β-LAP is referred to as a "small, latent TGF-β complex".

The role of LTBP in vivo is not completely clear. It has been found to be involved in the manufacture and secretion of TGF-β1 by a human erythroleukemia cell line. (Miyazono et al., EMBO J 10: 1091–1101 (1991)). The cDNA for the molecule has been cloned, and the protein contains several epidermal growth factor like repeats. See Kanzaki et al., Cell 61: 1051–1061 (1990); Tsuji et al., Proc. Natl. Acad. Sci. USA 87: 8835–8839 (1990). This feature is shared with many other molecules. An additional repeating structure is also found, which has 8 cysteine residues in one motif.

The structure of the LL-TGFβ1 complex has been analyzed in some detail, and is as described supra; however, the LL complexes of TGF-β2 and TGF-β3 have not been studied. Given the fact that the TGF-β2 and TGF-β3 molecules differ from TGF-β1, and that their associated "LAP" proteins differ, it would have been expected that there would be a binding protein specific to each form and differing from that associated with TGF-β1. Surprisingly, it has been found that the binding protein for both TGF-β2 and TGF-β3 is the same as that for TGF-β1. Isolated large latent complexes are thus described which contain (i) either dimerized TGF-β2 or TGF-β3, (ii) the B-LAP for the TGF-β2 or TGF-β3 form, and (iii) the LTBP molecule, which was previously associated only with TGF-β1. The complexes are useful as inactive forms of TGF-β2 and TGF-β3, which can be treated to yield the active TGF-β2 and TGF-β3 molecules.

The investigations described herein led to a surprising discovery in that an additional binding protein immunologically distinct from LTBP and having a molecular mass of about 150 KDa associates with all of TGF-β1, TGF-β2 and TGF-β3. This is referred to as "LTBP-2" hereafter. Thus, new complexes containing TGF-β1 are described, as well as a second form of isolated LL-TGF-β2 and LL-TGF-β3 complexes. All of the complexes described herein are characterized in preferred embodiments by a molecular weight of about 210 KDa as determined by SDS-Page.

These and other aspects of the invention are elaborated upon in the disclosure which follows.

DETAILED DESCRIPTION OF THE PREFERRED EMBODIMENTS

Example 1

Various cell lines are used in the experiments described infra. This example discusses the various conditions under which these were grown and cultured.

The different human glioblastoma cell lines used were cultured in Dulbecco's modified Eagle's medium, supplemented with 10% fetal bovine serum ("FBS" hereafter, and antibiotics (100 U of penicillin, 50 $\mu$g of streptomycin). The cells were kept in a 5% $CO_2$ atmosphere at 37° C.

The human foreskin fibroblast cell line AG 1518 is publicly available. This was cultured in Eagle's minimum essential medium supplemented with 10% FBS and the antibiotics listed supra.

Cell line PC-3 is a human prostate carcinoma cell line, and it was cultured in RPMI 1640 supplemented with 10% FBS and antibiotics.

To study the complexes, large amounts of conditioned medium from the cell line U-1240 MG, a human glioblastoma cell line, were required. Cell line U-1240 MG has been deposited at the Institut Pasteur Collection Nationale de Cultures de Microorganismes, 25, Rue du Docteur Roux, 75724—Paris Cedex 15, France, in accordance with the Budapest Treaty, and has been assigned Deposit Number I-1166. To achieve this, the cells were grown to confluence in roller bottles. These were then washed, three times, with phosphate buffered saline, and were then incubated in 50 ml of serum free Dulbecco's modified Eagle's medium (DMEM) per bottle. The medium was collected after two days. This procedure was repeated with three days of replenishment of the cells, using DMEM with 10% FBS between each collection. In an alternative protocol, the conditioned medium was harvested every two days over a six day period. The cells were then grown in DMEM with 10% FBS for one week. The collection scheme was repeated three times.

Collected conditioned medium, regardless of how secured, was centrifuged at 2000xg for 10 minutes, and the supernatants were stored at −20° C.

For other cell types, the conditioned media were collected on a much smaller scale. To that end, 175 $cm^2$ Falcon flasks were used, and DMEM plus 10% FBS was the medium. The atmosphere was 5% $CO_2$. For AG 1518 fibroblasts, the medium used was Eagle's minimum essential medium.

Example 2

Experiments were first carried out to determine if the various cell lines cultured were producing latent TGF-$\beta$ complexes. To do this, conditioned medium was collected from control cell line AG 1518, and four human glioblastoma cell lines (U-1240 MG; U-251MGO; U-251 MGSp; U-343 MGa Cl2:6). Conditioned media (500 ul; 4 ml/lane) was concentrated 50 fold using ultrafiltration in the presence of 0.1% SDS. These media had not been subjected to ammonium sulphate precipitation. The samples were then analyzed via SDS-gel electrophoresis. This analysis involved mixing the samples with SDS-sample buffer (100 mM Tris-HCl, pH 8.8, 0.01% bromophenol blue, 36% sucrose and 4% SDS) without reducing agents, and heating to 95% for 3-4 minutes. After this, the samples were applied to 5-18% polyacrylamide gels, in accordance with Blobel et al., J. Cell Biol. 67: 835-851 (1975) under non-reducing conditions. Following this, the sample was immunoblotted. First, it was electrophoretically transferred to a nitrocellulose membrane for 12-16 hours in the presence of 0.02% SDS. Following this, the blotted samples were contacted first with an antiserum against LTBP (Miyazono et al., EMBO J 10: 1091-1101 (1991), and then with antiserum against each of $\beta$1-LAP, $\beta$2-LAP, and LTBP. The antibodies were visualized using $^{125}I$ labeled protein A followed by autoradiography, in accordance with Miyazono et al., Biochemistry 28: 1704-1710 (1989).

Figure 1A:
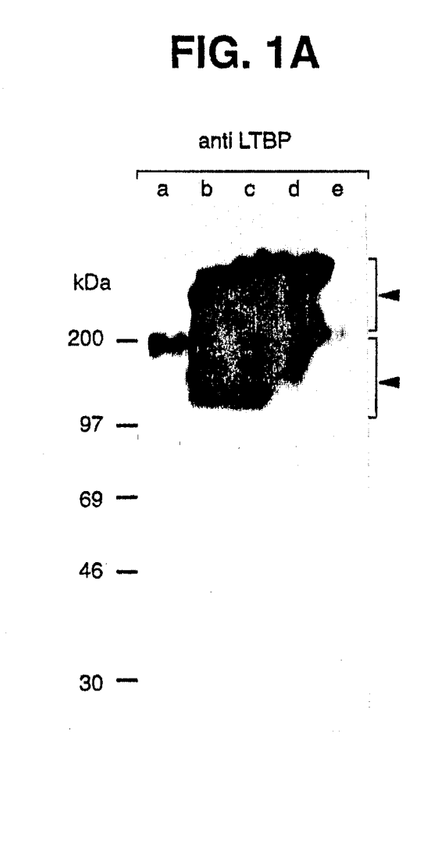
FIG. 1A shows the result of immunoblot studies on conditioned medium obtained from various human cell lines (glioblastoma and fibroblasts), using antisera to LTBP.
Figure 1B:
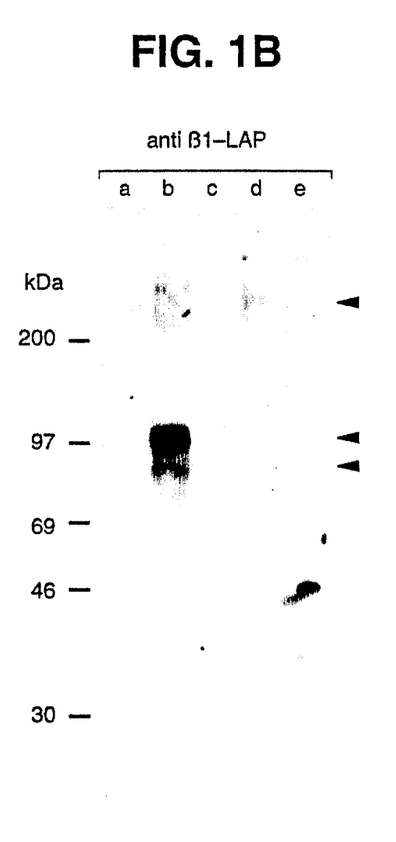
FIG. 1B parallels the study of FIG. 1A, using antisera to β1-LAP.
Figure 1C:
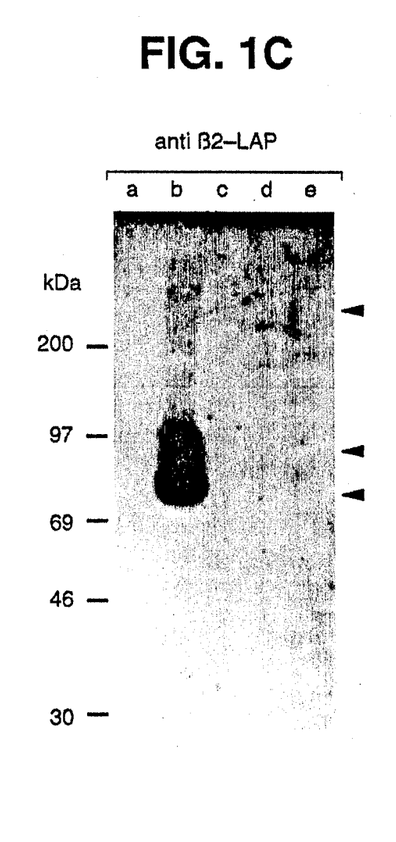
FIG. 1C parallels the study of FIG. 1A, but uses antiserum to β2-LAP.

The results of the immunoblotting, presented in FIGS. 1A, 1B and 1C, show that when LTBP specific antiserum was used, multiple bands corresponding to sizes between 100-200 KDa, and between 210 and 310 KDa were observed. This was true both for the fibroblast line AG1518, as well as for all glioblastoma lines.

When $\beta$1-LAP specific antisera was used, it showed the presence of TGF-$\beta$1 in large complexes of about 220 KDa, as well as small complexes (80-100 KDa), in conditioned media from U-1240MG and U-251 MGsp (panel 1B; lanes b and d, respectively). Panel 1C, which depicts experiments using $\beta$2-LAP antiserum shows that small or large complexes were seen only in U-1240 MG.

Comparable experiments were carried out using $\beta$3-LAP specific antisera. While these results are not shown, faint bands were found in all supernatants from all glioblastoma cell lines tested.

Interpretation of these data indicate that the larger bands in panel 1A most probably represent associations of LTBP with $\beta$-LAPs, with the smaller bands representing free LTBP.

Example 3

In order to assess the TGF-$\beta$1 activity of the conditioned media from the tested cell lines, inhibition of growth of mink lung epithelial cell line, CCL 664 was tested, using a $[^3H]$thymidine incorporation assay as described by Miyazono et al., EMBO J 10: 1091-1101 (1991). TGF-$\beta$ is known to inhibit the growth of this cell line.

Samples were concentrated 10 times using ultrafiltration. Total TGF-$\beta$ activity was determined after heating media to 80° C. for 10 minutes to activate any inactive TGF-$\beta$. Contribution of inhibitory activity not from TGF-$\beta$1 was estimated by assaying samples in the presence of a TGF-$\beta$1/TGF-$\beta$2 neutralizing antibody. (It is unknown if this antibody neutralizes TGF-$\beta$3). The contribution of activity which could not be neutralized with the antibody was about 10%, in both the active and non-active fractions.

The results, which are shown in Table 1, show that while U-251 MGO, U-251 MGsp and U-343 MGa Cl2:6 give similar activities, U-1240 MG gave much higher values, although there were large variations from batch to batch. The percent of TGF-β activity in U-1240 MG conditioned medium from active forms was found to be 26% while no active forms were found in the other lines.

These data suggested that U-1240 MG should be chosen for further studies of the structural properties of small and large latent TGF-β complexes, and the relationship between LTBP and TGF-β2.

TABLE I

| cell line | TGF-β activity (ng/ml) | (% active TGF-β) |
|---|---|---|
| U-1240 MG | 8 ± 7[a] | 26 ± 12[b] |
| U-251 MGO | 0.5 | <1 |
| U-251 MGsp | 0.6 | <1 |
| U-343 MGa Cl 2:6 | 0.6 | <1 |

[a]Data are expressed as means ± S.D., n = 6.
[b]Data are expressed as means ± S.D., n = 4.

Example 4

In order to characterize the different TGF-β complexes synthesized and secreted by U-1240 MG, the conditioned medium, collected as described in Example 1, was used. 3350 ml of conditioned medium was obtained, it was thawed, recentrifuged, and passed through siliconized glass wool. Following this, a solution of 95% ammonium sulfate was added, and the mixture was equilibrated at 4° C. overnight. This treatment results in a precipitated protein, which was recovered by centrifuging at 8000xg for 25 minutes. The resulting pellet was dissolved in 220 ml of 50 mM NaCl, 10 mM phosphate buffer, pH 7.4, then dialyzed against the same buffer, followed by filtration through siliconized glass wool and a 0.45 μm filter. The resulting solution (350 ml) was applied on to a Q-Sepharose column for chromatography. A flow-through portion resulted, as did eluents. The column was equilibrated with 50 mM NaCl, 10 mM phosphate, at pH 7.4, at a flow rate of 4 ml/min at 0° C. Elution was carried out using an NaCl gradient of from 50 mM to 1000 mM in 10 mM phosphate, pH 7.4 at a rate of 4 mM NaCl/ml and a flow rate of 2.5 ml/min. Eluents were collected in 5 ml fractions. The fractions were treated as indicated supra (i.e., subjected to SDS PAGE separation, but using as S-18% gradient gel), and were immunoblotted using the ECL Western blotting system. Antisera against each of β1-LAP, β2-LAP, β3-LAP and LTBP were used, leading to the patterns shown in FIG. 2B.

Figure 2A:
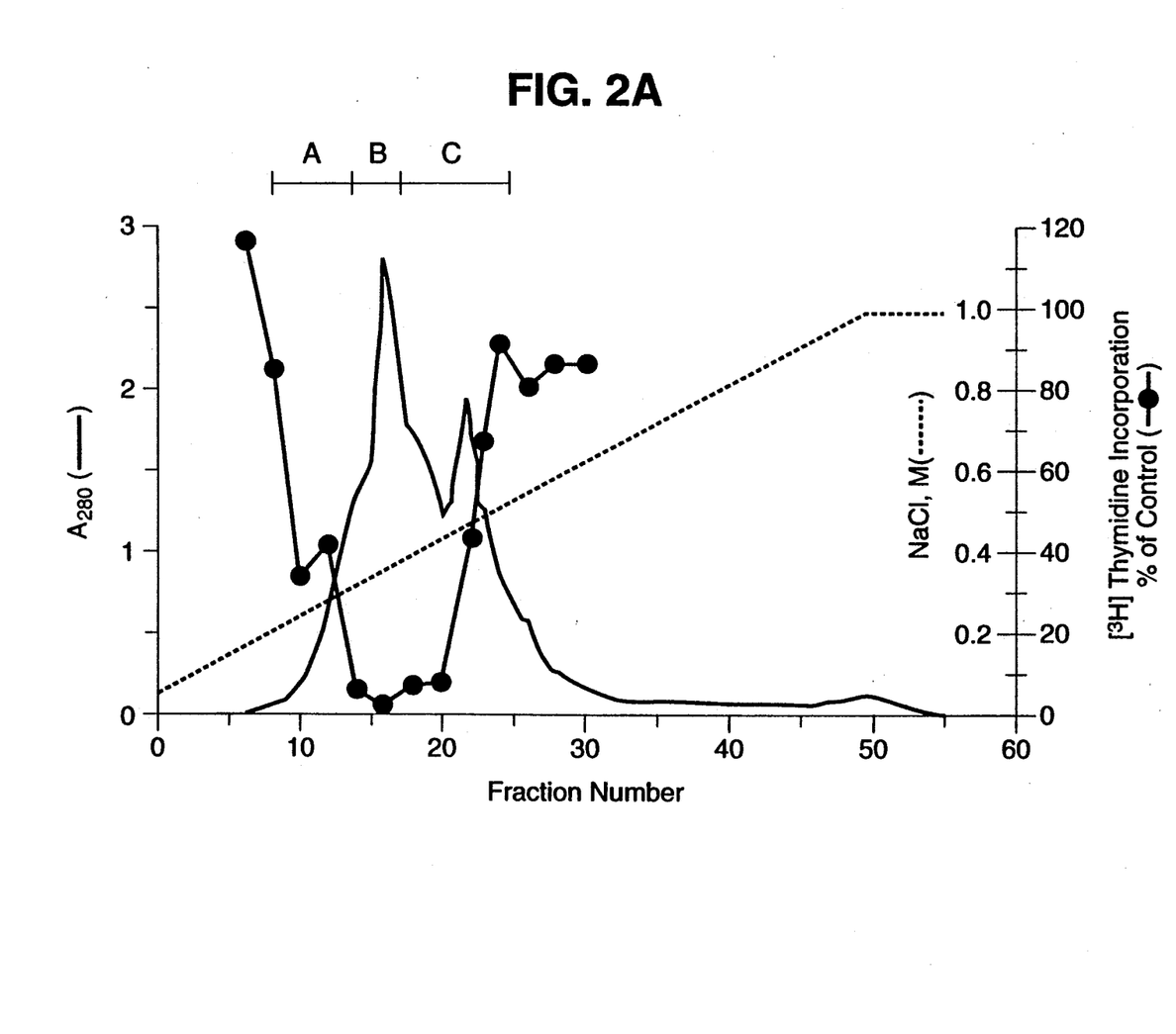
FIG. 2A presents ion exchange chromatography using a Q-Sepharose column and [$^3$H] thymidine incorporation data for TGF-β containing fractions of conditioned medium from glioblastoma cells.
Figure 2B:
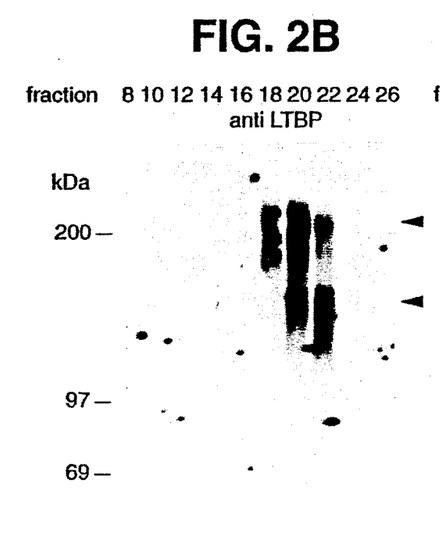
FIG. 2B, 2C, 2D and 2E depict immunoblot analysis ion exchange of chromatography eluents.

These results show that β1-LAP was found in fractions 14-22 at a size of about 210 KDa. The β2-LAP complex was also found in fractions 14-22, also as a large complex of about 210 KDa. A small complex was found in fractions 8-12, and having a mass of about 75 KDa.

As to β3-LAP, small amounts of 210 KDa large complex were found in fractions 14-20, together with small complexes of 74 KDa in fractions 10-12.

Figure 2C:
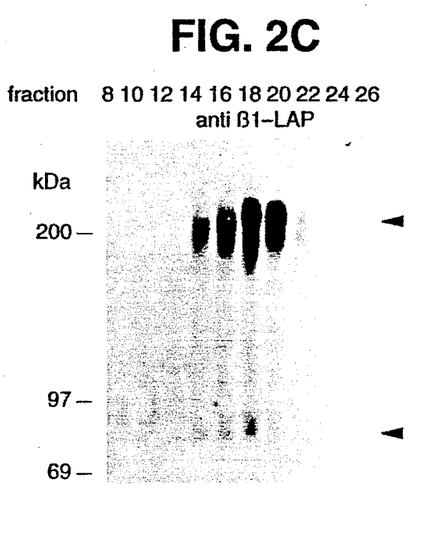
Figure 2D:
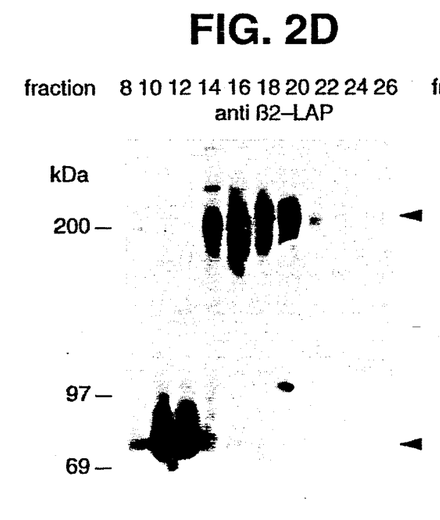
Figure 2E:
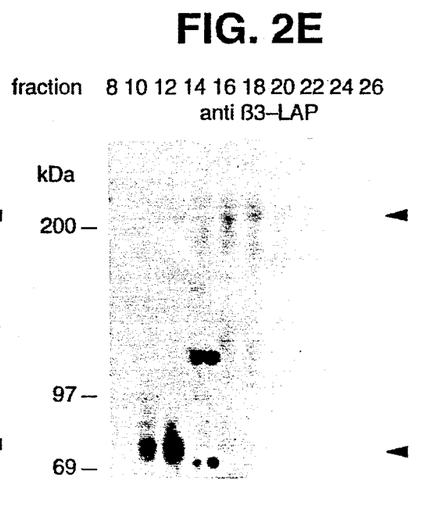
Figure 2F:
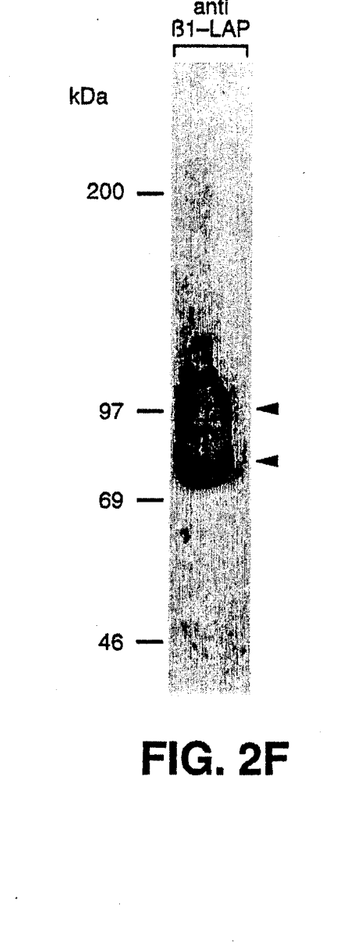
FIGS. 2F, 2G and 2H show analysis of flow through fractions of ion exchange chromatography.
Figure 2G:
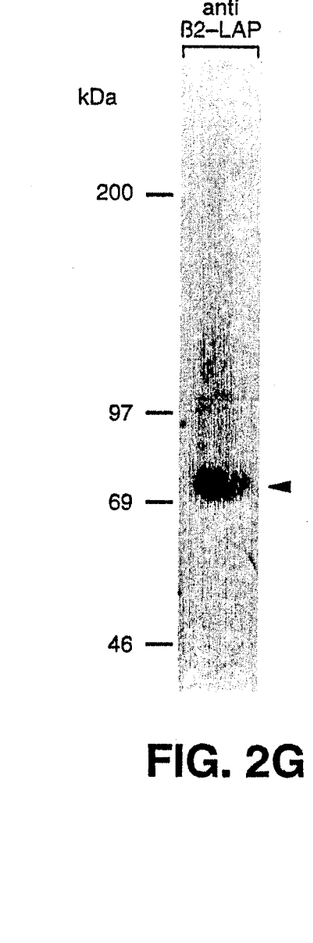
Figure 2H:
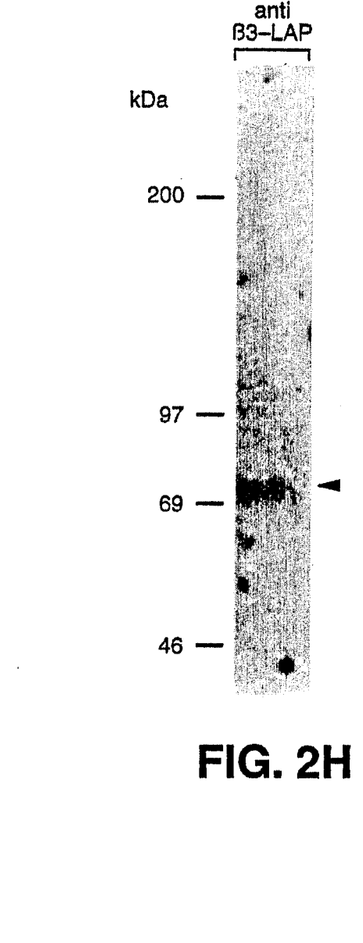
Figure 3A:
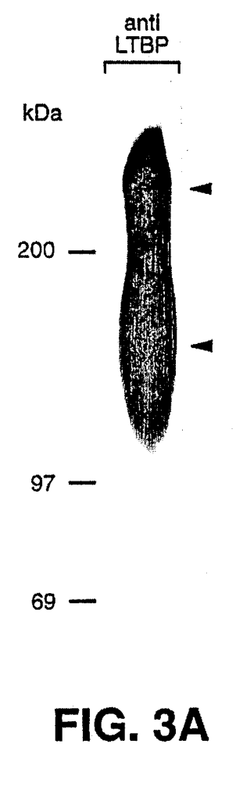
FIGS. 3A, 3B, 3C and 3D present data secured when a fraction of Sepharose eluent was applied to an anti-LTBP Sepharose column followed by immunoblotting using anti-LTBP (FIG. 3A), anti-$\beta$1-LAP (FIG. 3B), anti $\beta$2-LAP (FIG. 3C), and anti $\beta$3-LAP (FIG. 3D).
Figure 3B:
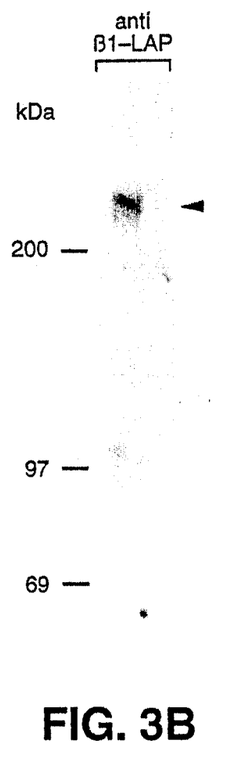
Figure 3C:
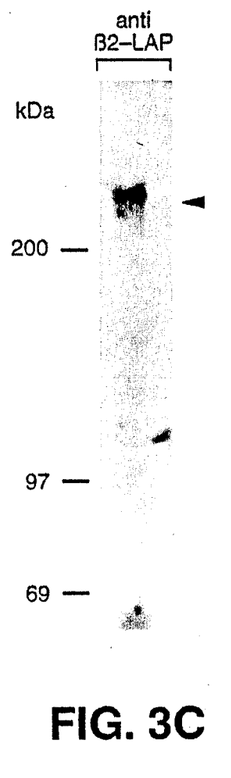
Figure 3D:
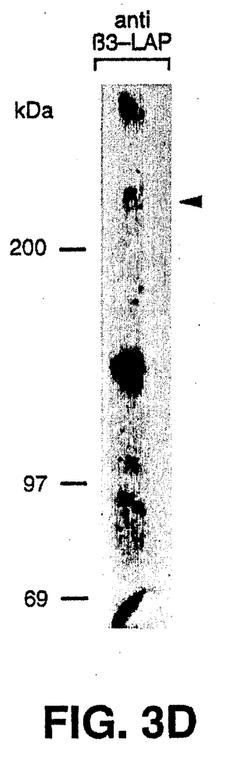

The flow-through portion of the test material was also immunoblotted, and these results are shown in FIG. 2C. 80 and 97 KDa forms were identified with anti-β-LAP. The 80 KDa form probably indicates a β1-LAP dimer. The 97 KDa entity is probably an unprocessed TGF-β1 precursor dimer, and/or a complex of β1-LAP and mature TGF-β1, held together by an anomalous disulphide bond.

With respect to TGF-β2, a small TGF-β2 complex of 75 KDa is found in the flow through fraction. Similarly, small TGF-β3 complexes were found in flow through.

As to LTBP, this was found in fractions 18-22 in 210 KDa complexes, and in a free form at a size of about 150 KDa in fractions 20-22.

Example 5

For further characterization fractions containing TGF-β activity were divided into four pools denoted A (fractions 8-13), B (fractions 14-16) C (fractions 17-22) and flow through.

Pool B interestingly contained large complexes but no LTBP, suggesting that TGF-βs in these fractions are covalently associated with other molecule(s) of similar size(s) as LTBP. Pool C (fractions 17-22) contained large TGF-β complexes with LTBP and LTBP in a free form (see FIG. 2B).

Experiments were carried out to determine the activity of the TGF-β material in each pool. The mink lung epithelial cell assay was used, as described supra, and the results are summarized in Table 2, which follows. To summarize, 30% of activity was found in the flow-through fraction, 12% in pool A, 19% in pool B, and 26% in pool C. The total recovery, compared to the medium prior to Q-Sepharose chromatography is 96%.

TABLE II

| materials | TGF-B (μg) | TGF-B (%) | protein (mg) |
|---|---|---|---|
| starting material Q-Sepharose | 53 | 100 | 410 |
| flow-through | 20 | 39 | 52 |
| pool A | 7 | 12 | 37 |
| pool B | 10 | 19 | 74 |
| pool C | 14 | 26 | 112 |

Experiments show that all three forms of β-LAP occur in so-called "small forms" of 75-97 KDa, and large forms of 210 KDa. TGF-β activity in conditioned medium is usually latent, suggesting that different forms probably represent small and large latent TGF-β complexes.

Example 6

The observation that large latent complexes did not necessarily contain LTBP merited further experimentation. Further purification of pools B and C by chromatography on a Mono Q column followed by chromatography on an alkyl Sepharose column showed that it was possible to obtain some further separation of the large latent TGF-B complexes containing LTBP, from those not containing LTBP, but a complete separation could not be obtained.

In order to investigate whether each one of the TGF-β isoforms could form large latent complexes with LTBP as well as with LTBP2 separation using LTBP Sepharose was employed. 500 ml of conditioned medium from U-1240 MG was subjected to Q-Sepharose chromatography as described supra with the exception that the material was not subjected to ammonium sulphate precipitation. Fractions in the salt gradient were assayed by immunoblotting with antisera against LTBP and β1-LAP. Fractions which contained large TGF-β complexes with LTBP (corresponding to pool C) and fractions containing large TGF-β complexes without LTBP (corresponding to pool B) were pooled separately.

The pool C was incubated with Sepharose beads, which had been previously coated with anti-LTBP antiserum. To make this material, immunoglobulin fractions of antiserum to LTBP was purified via chromatography on protein A Sepharose. After this, the immunoglobulin fraction was eluted with 100 mM citric acid, pH 3.0. About 50 mg of immunoglobulin was obtained using 10 ml of serum. The immunoglobulin was then dialyzed against phosphate buffered saline, followed by coupling to CNBr activated Sepharose. Approximately 17 mg of immunoglobulin was added per gram of these beads. Medium from pool C described supra was then incubated with 2.5 ml portions of the treated Sepharose. Beads were washed with 0.5M NaCl, 100 mM Tris.HCl, pH 8.0, and then with 0.15M NaCl, 10 mM Tris.HCl, pH 8.0. After this, bound protein was eluted by heating to 96° C. in the presence of 1% SDS, 20 mM Tris.HCl, pH 8.8. The eluted protein was concentrated via centricon 10, as described, and elution and immunoblotting as described supra was carried out using antisera to LTBP, β1-LAP, β2-LAP and β3-LAP. The results shown in FIG. 3 indicates that all TGF-β isoforms are present in large latent complexes associated with LTBP.

Pool B was then analyzed for the presence of a large latent complex containing a component distinct from LTBP. To this, pool B was incubated with anti-LTBP Sepharose, prepared as described supra. This absorbed any LTBP from the fraction. The unabsorbed fraction was then applied to SDS-gel electrophoresis using 5-15% gradient gel, followed by immunoblotting, also as described, and using the ECL detection system. As a positive control, free LTBP prepared from PC-3 cells conditioned medium was used.

Figure 4:
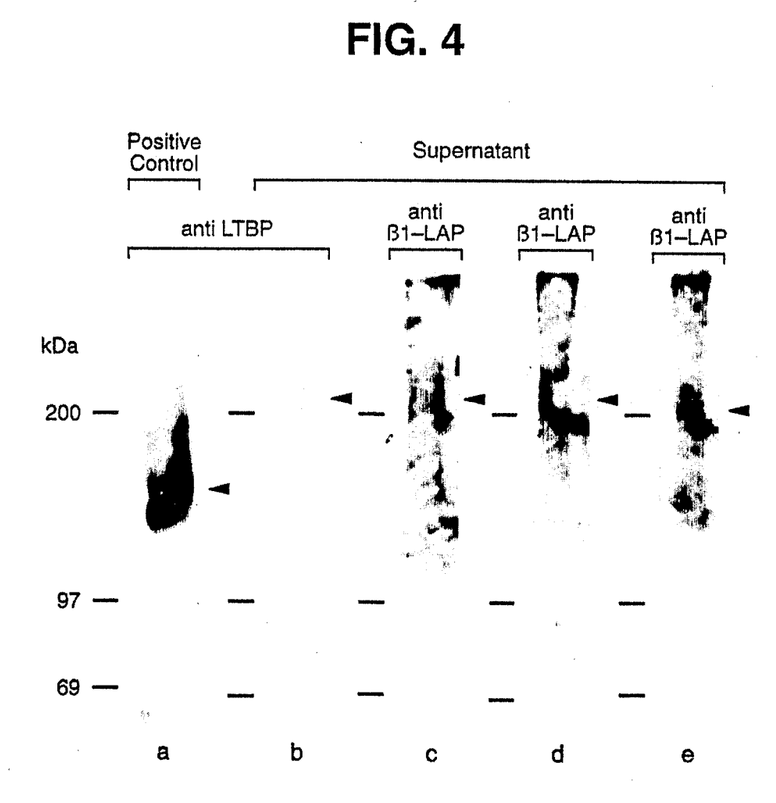
FIG. 4 shows analysis of a fraction of Q-Sepharose eluent which contains a component that is not LTBP, i.e. LTBP-2.

The results are shown in FIG. 4. Lane b shows that anti LTBP serum gave no indication of the molecule being present, while the PC-3 sample clearly shows free LTBP. When anti-β-LAP antisera were used, however, complexes of 205 kd were revealed, showing that each complex does in fact exist as a large latent complex with a molecule which is not LTBP, but which does have a molecular mass of about 150 kd.

Figure 5A:
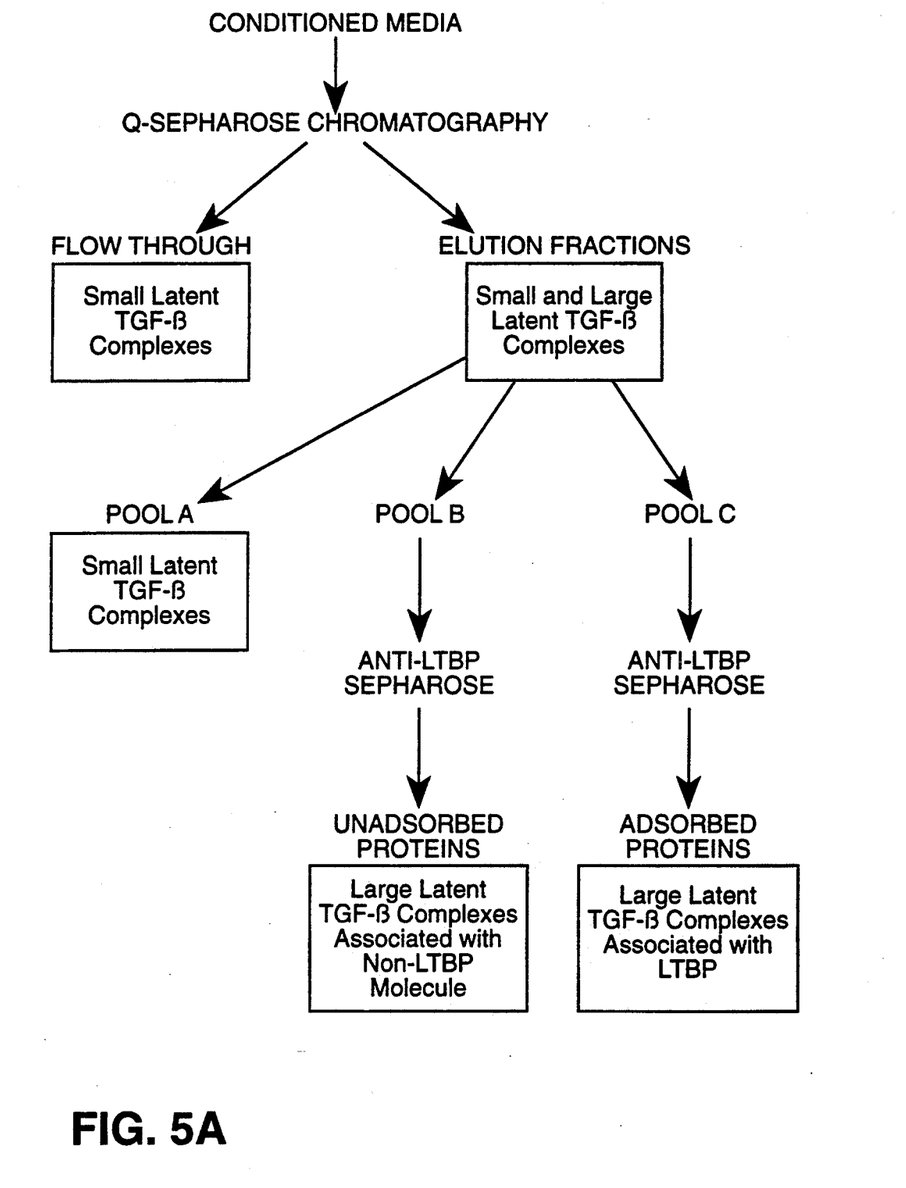
FIG. 5A schematically shows the purification protocol described herein.
Figure 5B:
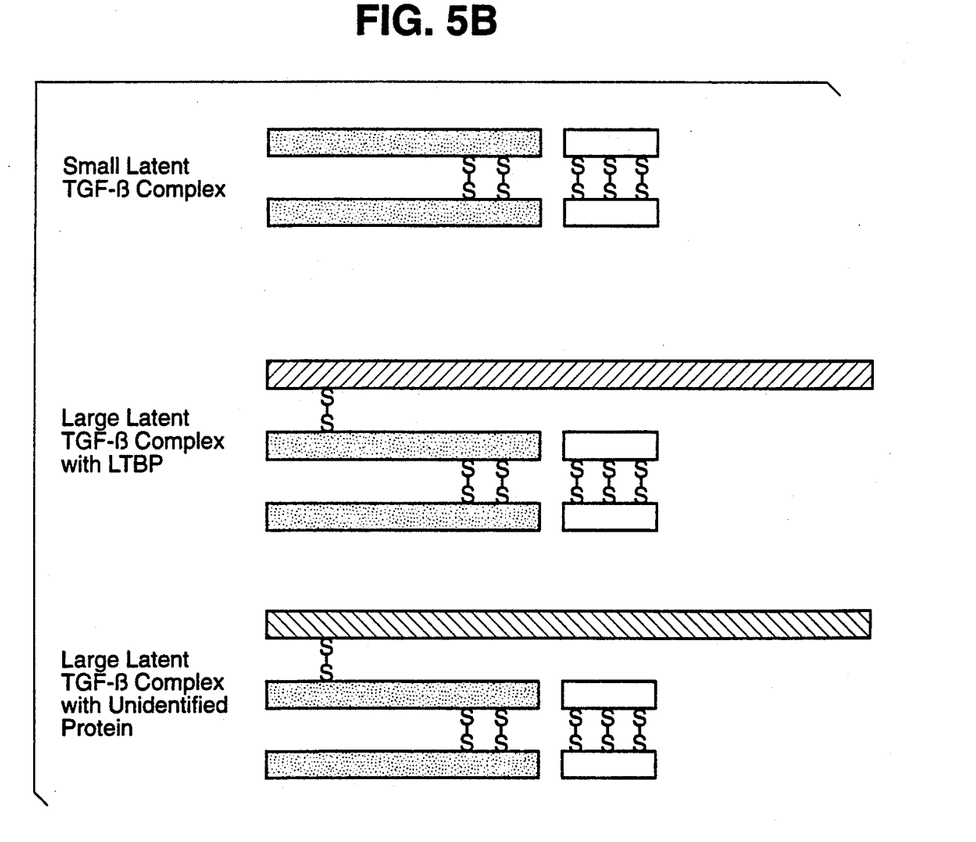
FIG. 5B presents molecular models of the small latent TGF-$\beta$ complex, the large latent TGF-$\beta$ complex with LTBP, and large latent TGF-$\beta$ complexes with the non-LTBP model.

A summary of the purification protocols described in these examples is presented in FIG. 5a, together with an indication of the species found in each fraction. FIG. 5b shows the derived structure of the various forms of TGF-β complexes discussed herein.

Several features of the invention are worth noting and are described here. First, it has unexpectedly been found that eukaryotic cells, such as human cell lines exist which produce large latent complexes of all TGF-β isoforms. "Large latent complex" as defined supra refers to a construct containing three parts: (i) the dimerized form of a TGF-β molecule, such as TGF-β1, TGF-β2 or TGF-β3, (ii) the latency associated protein or "B-LAP" molecule, and (iii) the latent TGF-β1 binding protein, or "LTBP". These cells and cell lines can also produce constructs where the third element is replaced by another moiety, discussed infra. When the cellular material is described as producing the stated TGF-β isoforms, such a statement does not preclude its production of complexes where the third moiety is replaced.

Human glioblastoma cell lines are preferred, in particular, cell line U-1240, MG, which has been deposited at the Collection Nationale de Cultures de Microorganismes (CNC M), Institut Pasteur, 25, rue due Docteur Roux, 75724 Paris Cédex 15, France, under Accession Number I-1166.

The identification of the complexes of β-LAP, TGF-β and LTBP molecules enables the skilled artisan to manufacture isolated complexes containing these. As has been indicated supra, complexes of TGF-β1, β1-LAP and LTBP are known, but it was not known, nor was it suggested, that TGF-β2 and TGF-β3, individually, associate with their corresponding β-LAP moiety and LTBP, previously believed to associate with the TGF-β1 form of the TGF-β molecule only.

The experiments have also identified new large latent complexes, wherein a TGF-β molecule, its associated LAP moiety, and a non-LTBP moiety associate. This latter moiety is characterized by a molecular mass of about 150 kd as determined by SDS-PAGE, and by being immunologically distinct from the recognized LTBP molecule. "Immunologically distinct" means that antibodies which are specific to LTBP do not bind to this non-LTBP molecule. This molecule is referred to as "LTBP-2" hereafter.

One can, of course, produce any of the complexes, as well as the isolated non-LTBP molecule by culturing the cell lines discussed supra, and then purifying the resulting complexes. This can be done via, e.g., contact with antibodies specific for the TGF-β component of the complex.

Other variations and modifications of the invention described herein will be clear to the skilled artisan and need not be elaborated upon herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated large latent TGF-62 complex consisting of:
   (i) latent, TGF-β1 binding protein;
   (ii) dimerized, beta latency associated peptide linked to said latent TGF-β1 binding protein via a disulphide bond, and
   (iii) dimerized TGF-β2 or dimerized TGF-β3 noncovalently associated with said dimerized beta latency associated peptide.

2. The isolated large latent TGF-β complex of claim 1, wherein said complex contains dimerized TGF-β2.

3. The isolated large latent TGF-β complex of claim 1, wherein said complex contains dimerized TGF-β3.

* * * * *